United States Patent
Kurfess et al.

(10) Patent No.: US 6,540,738 B2
(45) Date of Patent: Apr. 1, 2003

(54) APPARATUS FOR PROVIDING TRANSCUTANEOUS ACCESS TO AN INTERNAL HOLLOW ORGAN

(75) Inventors: Karlheinz Kurfess, Simmern (DE); Markus Salvermoser, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 109 days.

(21) Appl. No.: 09/733,525

(22) Filed: Dec. 8, 2000

(65) Prior Publication Data

US 2001/0007067 A1 Jul. 5, 2001

Related U.S. Application Data

(63) Continuation of application No. PCT/EP00/03170, filed on Apr. 10, 2000.

(30) Foreign Application Priority Data

Apr. 9, 1999 (DE) .......................................... 199 16 088

(51) Int. Cl.[7] .............................................. A61B 17/00
(52) U.S. Cl. ........................... 606/1; 606/108; 600/114; 604/513
(58) Field of Search ...................... 606/1, 108; 600/114; 604/539, 513, 533

(56) References Cited

U.S. PATENT DOCUMENTS

| | | | | |
|---|---|---|---|---|
| 4,069,826 A | | 1/1978 | Sessions et al. ............. 128/348 |
| 4,167,939 A | * | 9/1979 | Storz ............................. 600/114 |
| 4,670,008 A | | 6/1987 | Von Albertini ............... 604/165 |
| 4,685,901 A | | 8/1987 | Parks ............................ 604/96 |
| 5,073,166 A | | 12/1991 | Parks et al. ................... 609/93 |
| 5,122,122 A | * | 6/1992 | Allgood ........................ 604/105 |
| 5,127,393 A | * | 7/1992 | McFarlin et al. ............. 600/114 |
| 5,217,441 A | | 6/1993 | Shichman ..................... 604/283 |
| 5,279,575 A | * | 1/1994 | Sugarbaker ................... 604/104 |
| 5,312,351 A | | 5/1994 | Gerrone ........................ 604/117 |
| 5,358,488 A | | 10/1994 | Suriyapa ....................... 604/96 |
| 5,391,156 A | * | 2/1995 | Hildwein et al. ............. 411/503 |
| 5,465,710 A | * | 11/1995 | Miyagi et al. ................ 600/139 |
| 5,540,648 A | * | 7/1996 | Yoon ............................ 600/102 |
| 5,549,657 A | | 8/1996 | Stern et al. ................... 604/283 |
| 5,792,112 A | * | 8/1998 | Hart et al. .................... 604/164.01 |
| 5,814,026 A | * | 9/1998 | Yoon ............................ 604/539 |
| 5,855,569 A | | 1/1999 | Komi ............................ 604/280 |
| 5,857,999 A | | 1/1999 | Quick et al. .................. 604/107 |
| 5,865,817 A | * | 2/1999 | Moenning et al. .......... 604/164.01 |
| 5,941,815 A | * | 8/1999 | Chang .......................... 600/114 |
| 6,355,028 B2 | * | 3/2002 | Castaneda et al. ........... 600/201 |
| 6,440,061 B1 | * | 8/2002 | Wenner et al. ............... 600/114 |

FOREIGN PATENT DOCUMENTS

| | | |
|---|---|---|
| DE | 3782738 T2 | 12/1992 |
| DE | 69026883 T2 | 2/1996 |
| DE | 69303172 T2 | 1/1997 |
| DE | 19543011 | 5/1997 |

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

An apparatus provided for allowing transcutaneous access to an internal hollow organ, in particular the stomach. The apparatus comprises a tubular flexible probe, which can be placed transcutaneously in the hollow organ. The apparatus further comprises a rigid sleeve attachable to a section of the probe extending from the body. The sleeve engages around and guides the section. A clamping device is also provided for releasibly, but rigidly connecting the probe to the sleeve.

24 Claims, 10 Drawing Sheets

APPARATUS FOR PROVIDING TRANSCUTANEOUS ACCESS TO AN INTERNAL HOLLOW ORGAN

CROSSREFERENCE OF PENDING APPLICATION

This application is a continuation of pending international application PCT/EP00/03170 filed on Apr. 10, 2000 and which designates the US.

BACKGROUND OF THE INVENTION

The invention relates to an apparatus for providing transcutaneous access to an internal hollow organ, in particular to the stomach, comprising a tubular flexible probe disposable transcutaneously in the hollow organ of a living body, and a rigid sleeve attachable to a section of the probe extending from the body, such that the sleeve engages around this section.

Such an apparatus is disclosed in the German patent DE 195 43 011. In the known apparatus, a tubular flexible probe is introduced into the stomach and passed outwardly through the stomach wall and the abdominal wall. A retention ring at the opposite end of the probe prevents the probe from being extracted from the stomach. A reinforcing sleeve is applied to the section of the probe extending from the body, namely over its outer surface. As little relative shifting as possible should take place between the probe and the applied reinforcement sleeve, which probably results from frictional connection, although the document does not mention this.

The assembly comprising the probe section extending from the body and the reinforcement sleeve provides a transcutaneous access to an interior hollow organ, in this case the stomach. Instruments for example can be introduced into the body through this access. A valve element is provided at the outer end of the reinforcement sleeve to avoid release of the contents of the stomach or intestines or insufflation gas from the hollow organ.

A drawback of this apparatus is that relative motion between the probe section extending from the body and the applied sleeve cannot be excluded. Even if one provides a relatively good frictional connection between the outer surface of the flexible probe and the inner surface of the applied sleeve, it cannot be excluded that a relative movement takes place, for example when coughing which is undesirable.

This fixed frictional connection also greatly impairs the handling when applying the reinforcement sleeve to the probe. The reinforcement sleeve must be slid over the section extending from the body. With high friction, this is difficult and requires irregular sudden movements, so that it is difficult to subsequently correct the seating.

It is therefore an object of the present invention to provide an apparatus by which transcutaneous access can be accomplished in simple manner and with as little trauma as possible to the patient, in particular to ensure a reliable seating of the sleeve attached to the probe.

SUMMARY OF THE INVENTION

According to the present invention, this object is achieved in that a clamping device is provided for releasably, but securely connecting the probe to the sleeve, which comprises moveable clamping elements being moveable between a clamping and a non-clamping position.

The sleeve can be slid onto the probe section extending from the body without resistance and can be properly positioned, because the moveable clamping elements can be brought into a non-clamping position. A proper positioning is accomplished in that the probe is slightly drawn out so that its inner ring pushes the stomach wall onto the abdominal wall. After adjusting the proper and desired relative position between the probe and the applied sleeve, the clamping device is actuated and the moveable clamping elements are brought into the clamping position. The clamping effect can be selected such that no relative shifting takes place, even with sudden movements of the patient, for example when coughing.

A releasable, but fixed connection between the outer rigid sleeve and the probe section arranged therein is acheived through the clamping means, so that no relative movement between these two components is possible in clamped condition. The probe need only be cut off to the length of the apparatus, so that the instruments can be introduced via a sleeve-like element, as physicians are accustomed to with trocars. After removing the apparatus from the probe, a sufficiently long section remains extended from the body through which corresponding connections can be made for intragastral feeding or also other connecting elements. If necessary, the apparatus can again be attached to this section.

The probe is exactly aligned, because the sleeve engages around and guides the probe, such that it sits precisely concentrically in the rigid sleeve. The proximal, end face of the probe is also exactly circular, so that no danger exists that instruments can catch on the end edges during insertion, which could be the case if these were deformed to become oval or have another form. This represents a substantial contribution to the reliability of the apparatus.

In a further embodiment of the present invention, a base portion is provided for application of the apparatus to a body surface. The feature has the advantage that an exactly aligned seating of the apparatus is ensured on the body.

In a further embodiment, a valve assembly is provided through which the access produced by the probe is sealingly closed. The feature has the advantage that the apparatus itself comprises this valve assembly, so that no complicated connections need be made on the probe itself, rather the apparatus only needs to be placed upon or slid onto the probe.

In a further embodiment of the present invention, the clamping device comprises moveable clamping elements, which can be applied onto the outer side of the probe. The feature has the advantage that after slipping the apparatus onto the probe, the clamping elements can be applied to the outer side of the probe and a clamping between the apparatus and the probe can be accomplished.

In a further embodiment of the present invention, the moveable clamping elements can be applied over the surface of the outer side of the probe. The feature has the advantage that with the larger surface, a frictional connection is achieved even with a relatively small pressure, where the apparatus is clamped to the probe so as not to be shiftable in axial direction. The clamping device is non-distructive, without damaging the material structure, the form or the outside of the probe. This friction connection can then be enhanced by corresponding surface treatments or by the roughness of the clamping elements.

In a further embodiment of the present invention, the clamping elements include projections, which penetrate into the flexible probe when the clamp is closed, however without altering the lumen in the probe. The feature has the advantage that the projections ensure that the apparatus cannot release from the probe even by unskilled handling or with inadvertent catching of the apparatus on other instruments. With a corresponding flexible material, the projections can penetrate from the outside into the probe without altering the lumen in the probe, so that the entire inner cross-section is also available in the clamped condition as an instrument channel.

In a further embodiment of the present invention, the base portion is formed as a separate component. The feature has the advantage that the application of the apparatus is simplified in that the base is first slid onto the probe extending from the body and the base is then positioned and aligned at a suitable location on the body.

In a further embodiment of the present invention, the base comprises a clamping device. The feature has the advantage, especially combined with the above-mentioned features, that the base can be clamped after its alignment with the probe. Corrections can still be made, which are then easier for the operator to carry out than if the complete apparatus were attached.

In a further embodiment of the present invention, the clamping device comprises two approximately half-shell clamping elements. The feature has the advantage that these clamping elements can be arranged to save space, can engage around a large surface area of the probe and then encompass the probe in clamped condition to be aligned, sealed and supported.

In a further embodiment of the present invention, the clamping device comprises a cam shaft rotatable by an external lever, whose cam engages with at least one of the moveable clamping elements. The feature has the handling advantage that the apparatus can be applied with the clamping device being open, where the position of the lever clearly indicates this open position to the operator. After proper alignment, the lever only needs to be actuated to perform the clamping of the probe. The position of the actuated lever then clearly shows this condition to the operator.

In a further embodiment of the present invention, the base comprises a continuous, channel-like opening in which the clamping elements are arranged to be radially displaceable. The feature has the advantage that the clamping elements are integrated into the base in space-saving manner. The application or insertion of the probe in the open condition is simplified and the probe is clamped by a radial movement into the opening.

In a further embodiment of the present invention, the clamping device comprises a tube piece through which the probe is passed and the moveable clamping elements clamp the tube piece where the probe within the tube is clamped at the same time. This feature has the advantage that the clamping elements do not directly engage with the probe, but with the tube through which the probe is passed. A particularly gentle exertion of clamping force over a large surface results in that the entire tube piece is pressed onto the probe without damaging the probe. With appropriate selection of the surface of the tube material or even with the selection of the material itself, a special clamping effect is achieved which hinders through friction a relative movement between the tube piece and the probe therein.

In a further embodiment of the present invention, the base comprises a flat base plate. The feature has the considerable advantage that a larger surface is placed on the body surface via the base plate, so that the apparatus is properly supported, especially against tipping, on the body surface.

In a further embodiment of the present invention, the sleeve comprises a central channel whose diameter corresponds to the outer diameter of the probe. The feature has the advantage that the probe is exactly aligned and guided in the sleeve over its entire length, so that an exactly round and aligned inner instrument channel results, although the probe itself is made of a flexible material. Even if the probe has a slightly oval or distorted condition due to improper storage or because of excess use, it is again aligned to have an exactly round geometry when introduced into this channel. This ensures that an exactly cylindrical instrument channel results, despite such deformations.

In a further embodiment of the present invention, the sleeve can be closed at the proximal end with a valve assembly. The feature has the advantage that the valve assembly is arranged at a favorable position, also accustomed to operators of trocars, which simplifies the handling of the apparatus in the sense of a trocar sleeve.

In a further embodiment of the present invention, the sleeve comprises a head piece, disposable in sealing manner on the base portion. The feature has the advantage that the apparatus comprises two parts, so that the base portion can initially be applied and clamped to the probe and the headpiece is subsequently attached in sealing manner. After applying the base and clamping with the probe, it is easy to cut off the probe to the corresponding length, then slide on the headpiece, which carries the actual sleeve, and seal the connection Corrections are also possible by simply removing the headpiece, for example if the probe has not been cut off to the proper length.

This feature also simplifies the handling. The handling is also simplified when removing the apparatus after an operation. Initially, the head piece can be removed, where the free section of the probe then extends from the base. This section can then be grasped to ensure that the probe is not inadvertently drawn into the body when withdrawing the base.

In a further embodiment of the present invention, the sleeve comprises an inner tube which can be inserted into the flexible probe. The feature has the advantage that the flexible probe is not only supported and reinforced from the outer sleeve, but additionally through the inner tube inserted therein.

The inner tube additionally protects against the inner space of the flexible probe from being restricted under strong clamping pressure. A higher clamping pressure can then be exerted, such that the material of the flexible probe between the stiff inner tube and the stiff outer sleeve cannot be displaced. This embodiment is of advantage, for example when it is recognized from the beginning that the patient is unsettled or frequently coughs, for example due to smoker's cough.

In a further embodiment of the present invention, the inner tube extends from the distal side of the base. This feature has the advantage that the inner tube not only reinforces the flexible probe in the section projecting from the body, but also for example into the abdominal wall.

In a further embodiment of the present invention, the inner tube projects to the extent that it reaches into the internal hollow organ. This feature has the advantage that regions of the probe also in the internal organ are exactly aligned in the direction of the inner tube and therefore an exact insertion of stiff instruments is allowed. It can be prevented that the flexible probe directly after entry into the internal organ is bent or deflected out of alignment with the sleeve, for example when the patient turns, which would make the insertion of an instrument more difficult with such bent sections.

In a further embodiment of the present invention, the inner tube extends to a head piece of the apparatus. The feature has the advantage that a straight channel, exactly defined in its inner diameter is formed from the head piece, i.e. the proximal end region of the apparatus where an instrument is inserted. With this inner channel, the instruments can be exactly guided which considerably simplifies the handling, especially the insertion into the probe.

In a further embodiment of the present invention, the moveable clamping elements are biased in the clamping direction and an actuator element is provided through which the clamping elements are moveable into the non-clamping position. This feature has the advantage that the clamping elements as well as the actuator element, in the non-actuated condition, are urged into the clamping position, so that a non-releasable seating of the apparatus on the probe is guaranteed. Should the apparatus then be shifted axially with respect to the probe, the actuator element is actuated and the clamping elements are moved against their biasing, so that the sleeve can be shifted axially with respect to the probe.

This simplifies the handling, because the apparatus can initially be positioned on the abdominal wall relatively loosely, while the clamping elements then provide the mentioned non-releasable seating after releasing the actuator element. Other manipulations can then be carried out at this time, for example cutting off the probe. Finally, the relative seating can be corrected or the probe can be manipulated to exactly position the stomach at the inner side of the abdominal wall.

In a further embodiment of the invention, a fixing device is provided to secure the moveable clamping elements in their clamping position. The feature has the advantage that the mentioned simple handling is made possible, and on the other hand, the fixing device ensures that the moveable clamping elements are fixed in their clamping position. Desired or undesired manipulations on the actuator element then do not result in an inadvertent release of the sleeve from the probe.

In a further embodiment of the present invention, the fixing device comprises a fixing ring which fixes the moveable clamping elements in one angular position and allows rotation in another angular position. This feature has the advantage that the fixing device can be brought into the fixed position or the released position by simple angular movement.

In a further embodiment of the present invention, the base comprises two shell elements rotatable with respect to one another, where one of the shell elements carries the fixing ring. The feature has the advantage that the relatively large shell elements offer a convenient grasping location, for example with the hand of the operator, to carry out the angular movement of the fixing device.

In a further embodiment of the present invention, the clamping elements are arranged on components biased with springs to move toward the probe and the actuator element engages with these components such that the actuation of the actuator element moves the clamping elements against the force of the springs away from the probe. This feature has the advantage that the clamping elements can be moved in a simple procedure, namely by actuating the actuator element.

In a further embodiment of the present invention, at least one window is provided in the headpiece through which the assembly of the probe and the headpiece is visible. This feature has the advantage that the exact seating and the exact assembly, especially in the embodiment with the inner tube, can be visually inspected through the window.

It will be understood that the above-mentioned features and those to be described below are not only applicable in the given combinations, but may also be present in other combinations or taken alone without departing from the scope of the present invention.

BRIEF DESCRIPTION OF THE DRAWINGS

The invention will be described in more detail below in terms of selected embodiments in conjunction with the attached drawings.

DETAILED DESCRIPTION OF PREFERRED EMBODIMENTS

Figure 1:
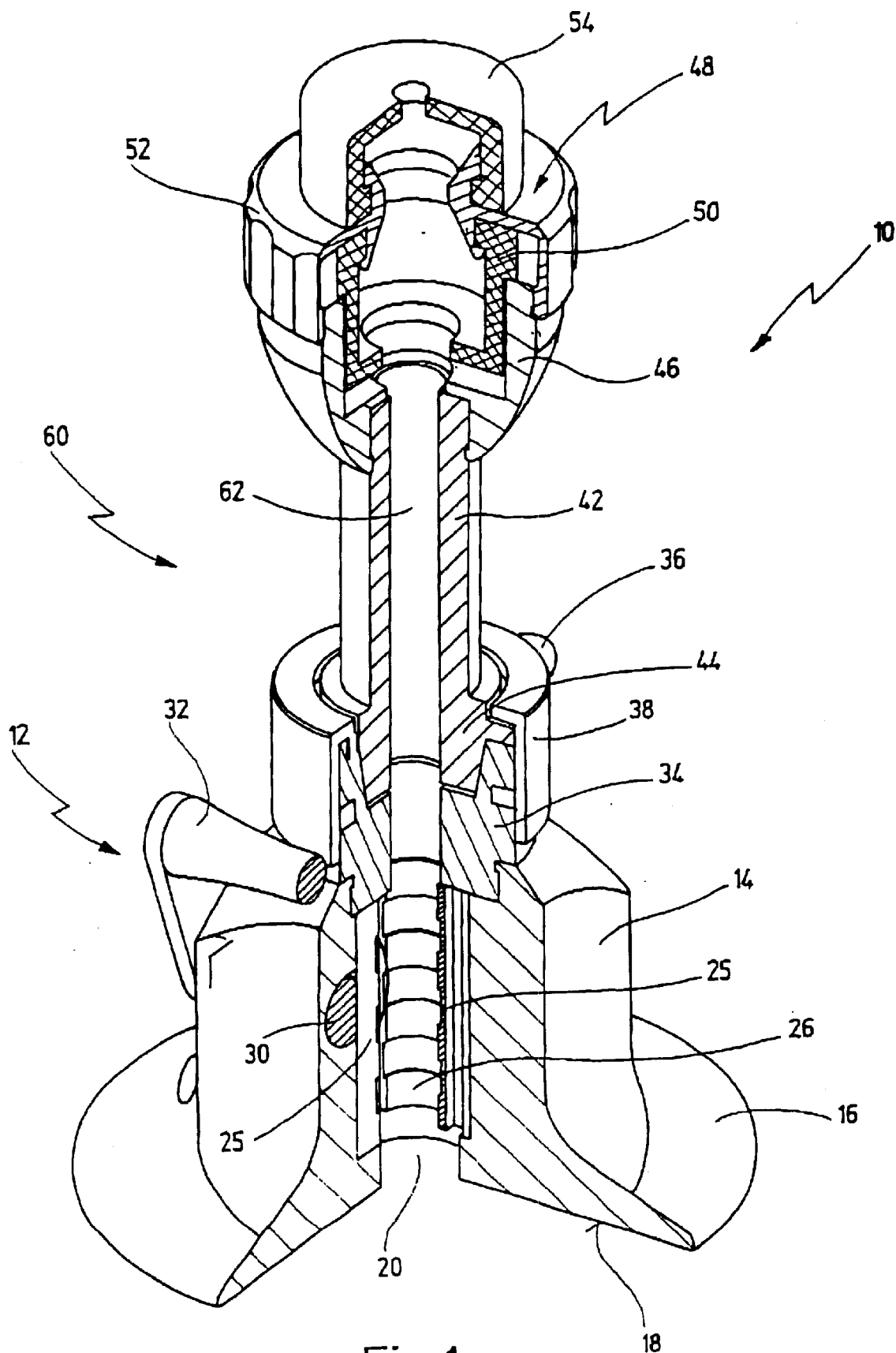
FIG. 1 shows a perspective view in partial cross-section of a first embodiment of the apparatus.
Figure 2:
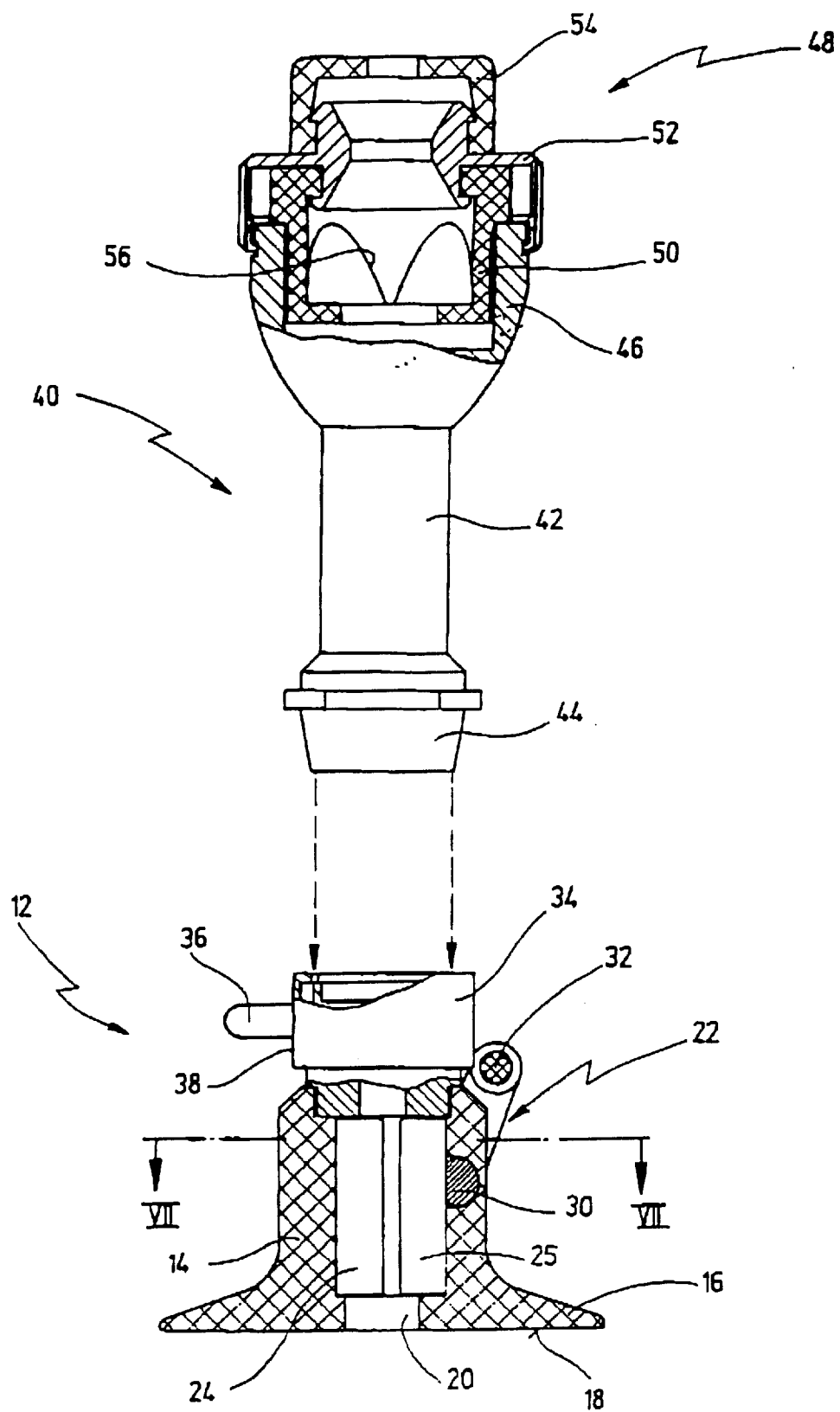
FIG. 2 shows an exploded view in partial longitudinal cross section of the apparatus of FIG. 1, where the headpiece is removed from the base.

FIGS. 1 and 2 illustrate an apparatus for providing transcutaneous access to an internal hollow organ, namely the stomach, and is designated with the numeral 10.

The apparatus 10 comprises a base portion 12, as is better seen in the illustration of FIG. 2. The base 12 comprises an approximately hollow cylindrical body 14, which joins into a base plate 16 of larger diameter.

The apparatus is placed on a body surface, for example the abdominal wall at the approximately disk-shaped underside 18 of the base plate 16, which will be described in more detail below.

A continuous channel-like opening 20 passes through the base 12. A clamping device 22 is arranged in the base 12. The clamping device comprises two clamping elements 24, 25, each having the form of half shells of a cylinder. The clamping elements 24, 25 are provided with projections 26 on the inner side, i.e. the side facing the channel-like opening 20.

The two clamping elements 24, 25 are produced by cutting a cylindrical tube provided with an inner threading along its length in two approximately equal half shells. The inner threading then represents the projections 26.

At its outer side, the clamping element 25 contacts a cam 30 of a cam shaft 28, which is pivotal through a lever 32. The function of the clamping device 22 will be described in more detail later in conjunction with the function of the apparatus 10, particularly in conjunction with the cross-sectional views of FIGS. 7 and 8.

The hollow cylindrical body 14 is provided with a coupling 34 at the end opposite to the base plate 16. The coupling 34 is formed as a quadruple coupling and comprises an outer ring 38, which can be grasped and rotated by hand via a pin 36. The coupling 34 has the purpose of coupling the base 12 to a headpiece 40 in sealing manner.

The headpiece 40 comprises an elongated hollow cylindrical shaft 42, having a coupling cone 44 arranged at its lower end as seen in FIG. 2, which fits into the coupling 34 of the base 12. At the end opposing the coupling cone 44, the shaft 42 is provided with a head 46, which supports a valve assembly 48. A screw cover 52 can be screwed onto the head. The screw cover 52 supports a lip valve 50 at its underside toward the head 46. In addition, an end sealing cap 54 made of rubber-elastic material is disposed on a central flange.

As can best be seen in FIG. 2, an inner valve flap 56 is present which seals the head 46 against the surroundings. The valve flap 56 however is slitted, so that an instrument can be inserted into the shaft 42 through the cap 54 by spreading of the valve flap 56 as will be described below.

After assembly of the base 12 and the headpiece 40 as shown in FIG. 1, a rigid sleeve 60 results having a continuous central channel 62.

Figure 3:
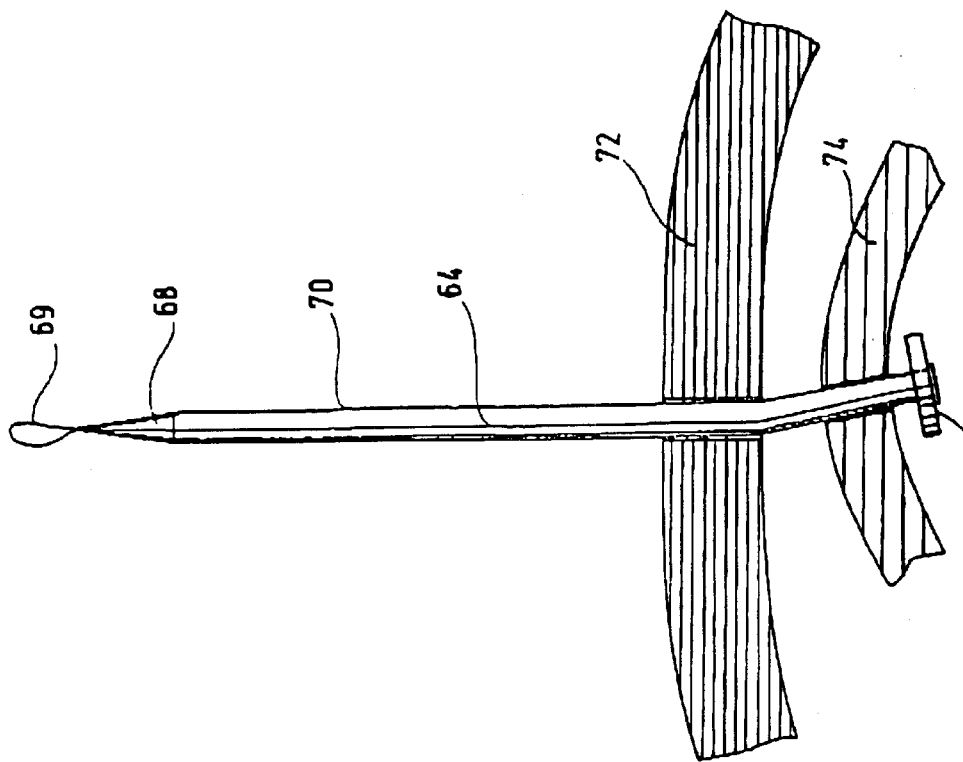
FIG. 3 shows an intermediate stage when the applying the apparatus to the human body, namely a condition in which a stomach probe has been passed through the stomach wall and the abdominal wall.

A probe 64 (see FIG. 3) consists of a hollow tube 70 of flexible plastic material having a retention ring 66 provided at one end. A cone 68 with a fixing loop 69 is provided at the opposite end. Such probes are known as probes for intragastral feeding. FIG. 3 shows a condition after the probe 64 has been inserted into the stomach via the esophagus and has been passed through the stomach wall 74 and the abdominal wall 72 to the outside.

This condition is accomplished as follows: A gastroscope, i.e. a flexible endoscope, is passed through the esophagus into the stomach and the stomach is inflated by insufflation. The tip of the gastroscope is pivoted and led to the location on the inside of the stomach wall 74 where the probe is to penetrate. This is recognizable from the outside, since this location is illuminated from the inside by the gastroscope. By darkening the room, this location for puncture can be seen from the outside. After sterile washing of the intended puncture region, a point incision of about 4 to 5 mm width is made. A corresponding canula is passed into the stomach under endoscopic control and the puncture needle is then removed. A carrier for a thread is placed on the plastic canula and the thread is introduced into the stomach.

As soon as the thread introduced into the stomach is visible in the gastroscope, the thread is grasped with a biopsy clamp and drawn together with the gastroscope out of the body through the mouth.

The proximal end of the thread is now tied with a knot to the fixing loop 69 of the probe 64. By slowing pulling the distal end of the thread, the probe 64 is drawn into the stomach. When the probe tip enters the plastic canula still placed in the abdominal wall, a slight resistance is felt. The probe 64 is then drawn out through the abdominal wall 72 with the plastic canula until the retension ring 66 engages the inner side of the stomach wall 74. This condition is shown in FIG. 3.

Figure 4:
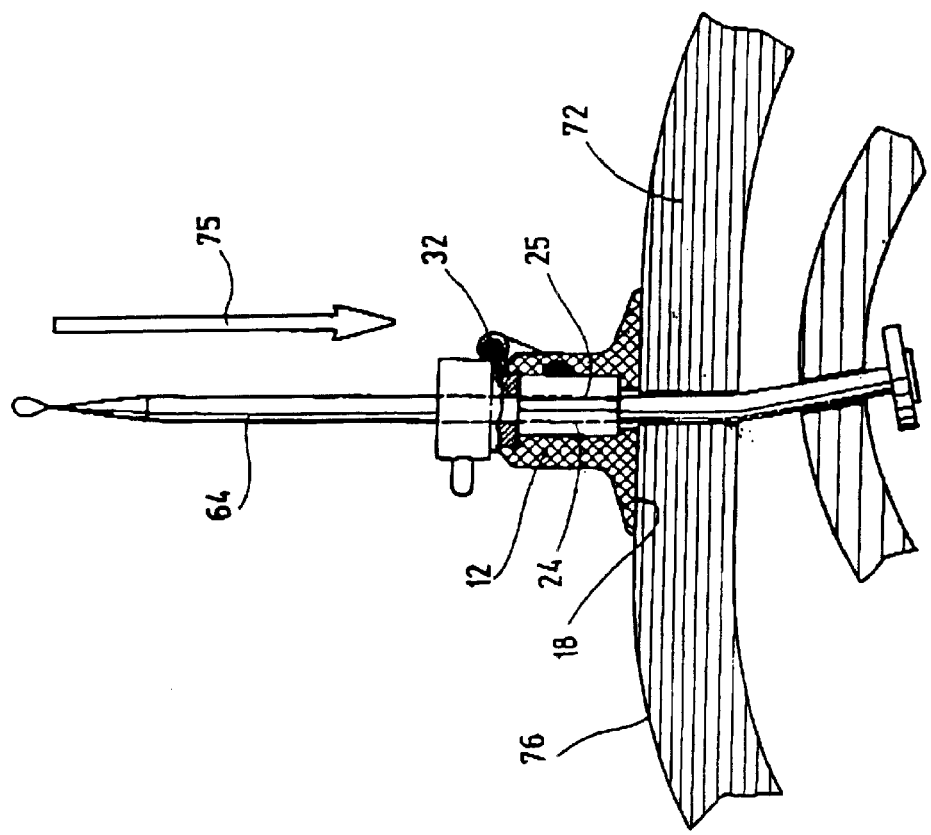
FIG. 4 shows an illustration comparable to FIG. 3 after a base of the apparatus of FIG. 1 has been placed on the end section of the probe extending from the body.

The apparatus 10 is disassembled in its parts, namely the base 12 and the headpiece 40. Base 12 is now pulled over the probe 64 extending from the abdominal wall 72 as shown in FIG. 4 with the arrow 75. The probe 64 is feed through the channel-like continuous open 20. The clamping device at this time is in its open position, i.e. the two clamping elements 24, 25 are separated from one another, as is illustrated in the cross-section of FIG. 7.

Figure 5:
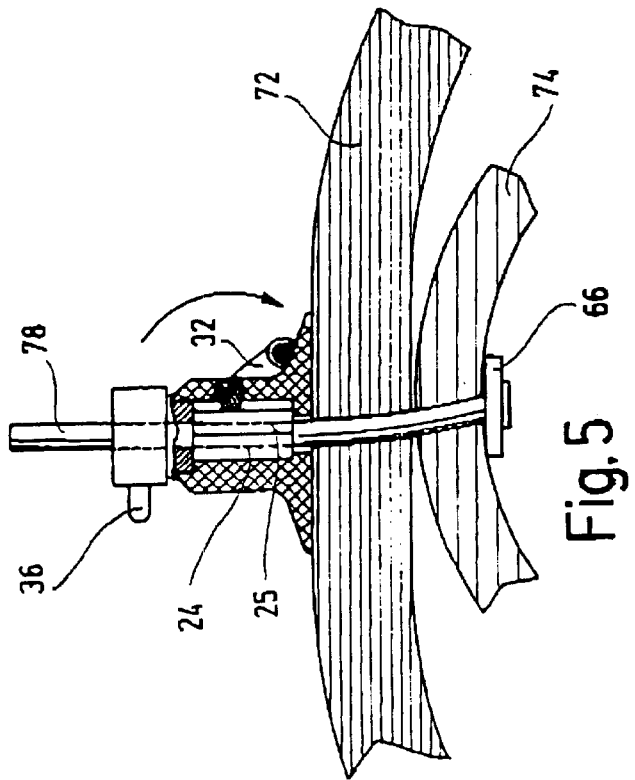
FIG. 5 shows an illustration comparable to FIG. 4 after the clamping procedure and after cutting off the probe.

The base 12 is pushed down until its base plate 16 lies on the outside 76 of the abdominal wall 72, as is shown in FIG. 4. The probe 64 is now grasped at the region extending beyond the base 12 and is pulled out until the retention ring 66 sits firmly against the inner side of the stomach wall 74 and the stomach wall 74 is drawn onto the inside of the abdominal wall 72, as shown in FIG. 5. The clamping device 22 is now actuated by operating the lever 32 as shown by the arrow in FIG. 5, where the base 12 is then clamped to the probe 64.

Figure 7:
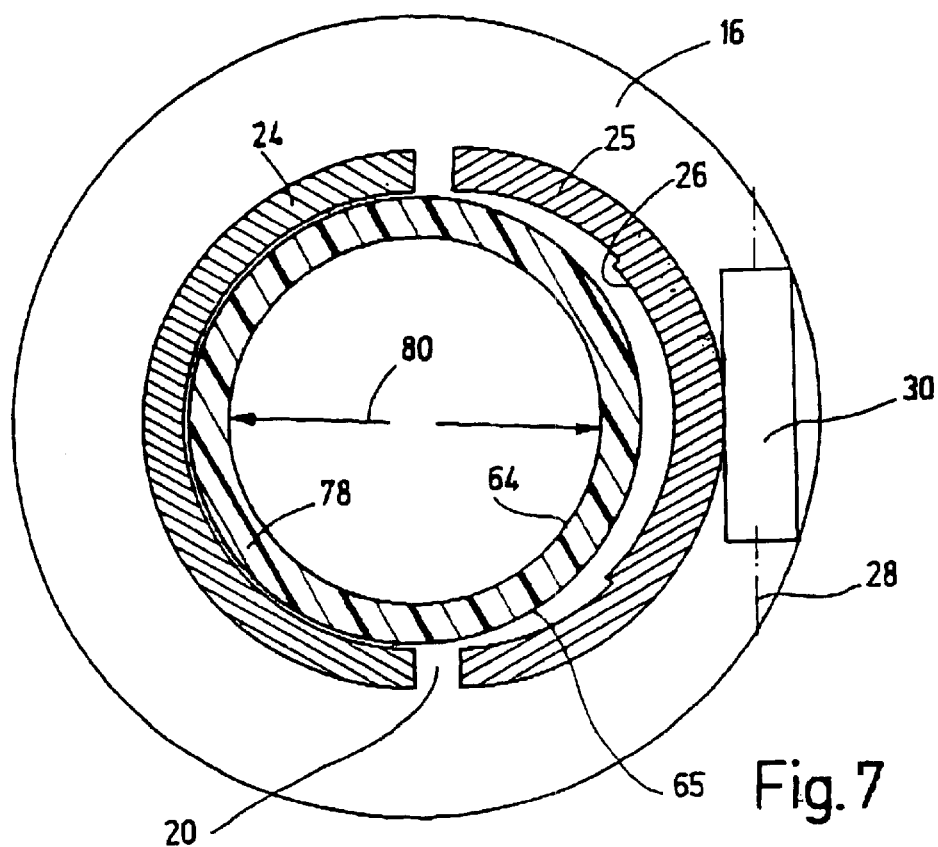
FIG. 7 shows a cross-section along the line VII—VII in FIG. 2 with the inserted probe before clamping.
Figure 8:
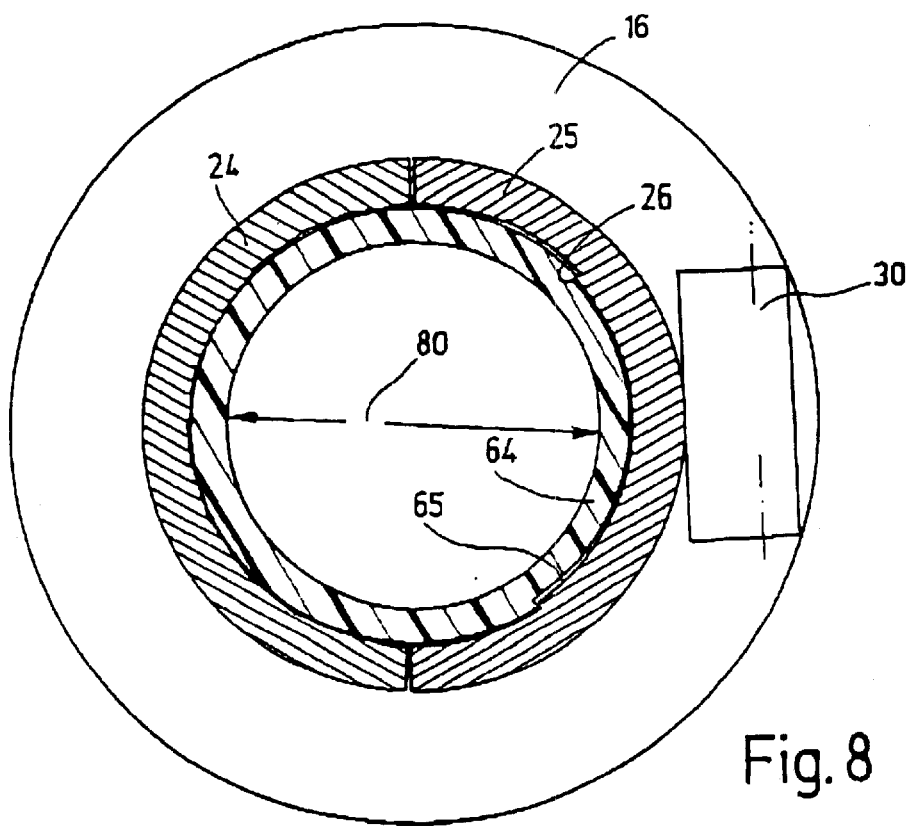
FIG. 8 shows an illustration corresponding to FIG. 7 after clamping.

As can be seen in the transition from FIG. 7 to FIG. 8, the approximately half-cylindrical shell of the clamping element 25 is moved toward the opposed clamping element 24 by the cam 30, whereby a closed circular channel 62 is formed in which the section 78 of the probe 64 extending from the body is received.

The projections 26 on the inner side of the clamping element 25 penetrate into the outer side 65 of the probe 64, however, without deforming the same so that its lumen or its inner diameter 80 is not altered or impaired.

As can be best seen in the cross-sectional view of FIG. 8, the section 78 of the probe 64 is seated to be exactly round and aligned between the clamping elements 24, 25. In this clamped condition, the clearance inner diameter of the channel 62 formed by the half shell clamping elements 24, 25 corresponds to the clearance outer diameter of the probe 64.

After fixing the probe 64, the section 78 extending from the abdominal wall is cut off, namely to a length which exactly corresponds to the length of the central channel 62 of the shaft 42.

The headpiece 40 is pushed onto the section 78 of the probe 64 in the same direction as the previous base 12, up to where the coupling cone 44 engages in the coupling 34 of the base 12. By rotating the ring 38 via the tab 36, the coupling is closed so that a sealing connection is achieved between the base 12 and the headpiece 40.

Figure 6:
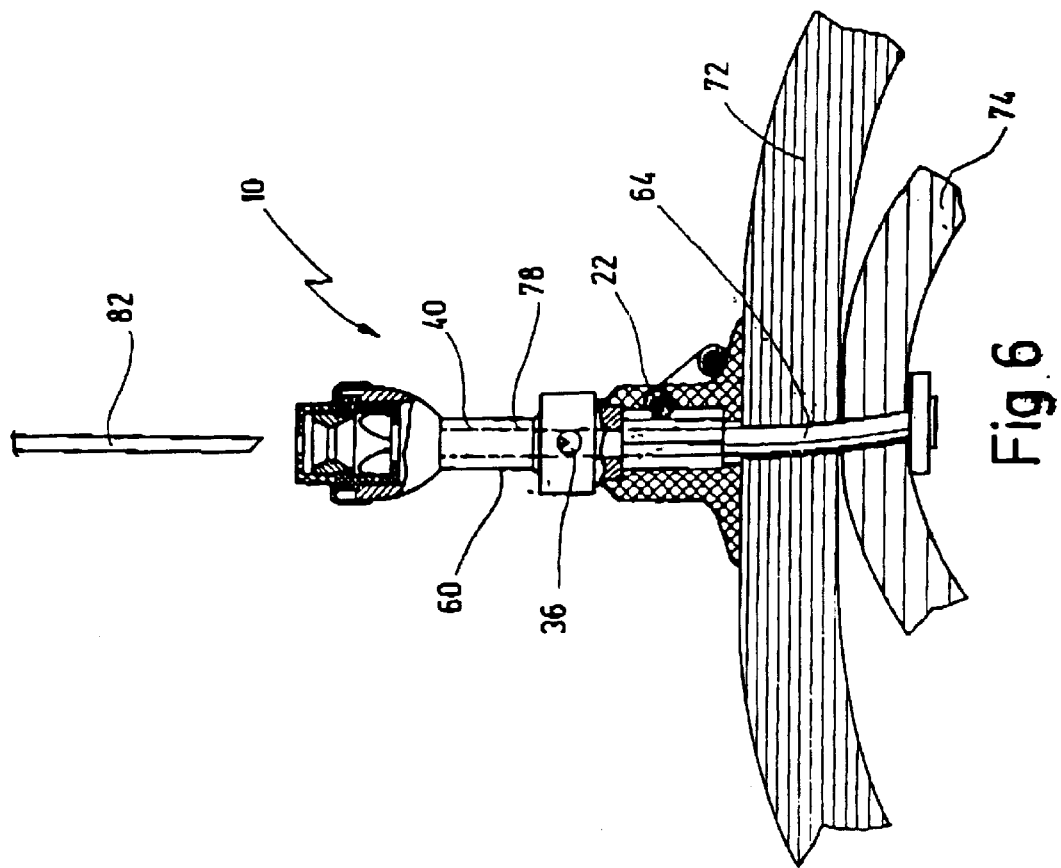
FIG. 6 shows the final mounted condition of the apparatus, where the headpiece has been placed on the base and where it is shown how an instrument is inserted into the apparatus.

In this manner, a continuous cylindrical channel 62 is created from the base plate 16 to the lip valve 50, whose clearance inner diameter exactly corresponds to the outer diameter of the section 78 of the probe 64. The outer end of the section 78 thus extends just up to the lower end of the lip valve 50. A sealed connection is created against the surroundings. In the assembly as shown in FIG. 6, instruments 82 can now be inserted through the head 46, for example an endoscope or surgical instruments to perform surgical procedures in the stomach or simply to make investigations.

When the procedure is completed, the coupling 34 is released, the headpiece 40 removed and the probe 64 is grasped at the section extending from the base 12. The clamping device 22 is then released by operating the lever 32, so that the base 12 can be raised to the extent that the probe 64 can be grasped between the underside 18 of the base plate 16 and the abdominal wall 72. After withdrawing the base 12, a luer-lock can be applied to the end section, through which nourishment can be fed to the stomach. The probe 64 then serves the purpose of intragastral feeding.

Should a further operative procedure or a further inspection be necessary, the luer-lock is removed and the apparatus 10 is applied again as described above. The procedure can be repeated several times over days or weeks, where it is only necessary to have the single incision, i.e. the incision through which the probe 64 is passed. This has the consequence of greatly reduced traumatization to the patient, since both feeding and also operative procedures can be carried out through the same probe 64.

A further embodiment of the present apparatus is shown in FIGS. 9 to 15 and generally designated with the numeral 90. The apparatus 90 comprises a base 92 and a headpiece 94.

The headpiece 94 comprises an approximately cylindrical body 96, whose outer circumferential wall is provided with two diametrically opposite windows 98, 99. A screw cover 100 is screwed onto the upper end, which is closed at the proximal side with a silicone cap 102. Corresponding valve flaps are arranged in the interior of this region, as described above, which provide a tight seal at the proximal end when no instrument is present in the apparatus 90.

The headpiece 94 is provided with an inner tube 104, which extends to the region of the screw cover 100. As can be seen from the exploded view in FIG. 10 and the assembled view in FIG. 9, the inner tube 104 has a length such that it extends from the underside of the base 92.

The outer diameter of the inner tube 104 is dimensioned such that it corresponds to the inner clearance diameter of the probe 106, which is to be inserted into the apparatus 90. The apparatus 90 can be inserted, or said in another way, the probe 106 can be pushed onto the assembly such that the probe 106 reaches the region of the view windows 98, 99, which can be monitored visually.

The base 92 consists of two half shells 108, 110 placed together somewhat in the form of a canister. The upper half shell 108 shown in FIGS. 9 and 10 comprises a central opening 112, whose cross-section is dimensioned such that the probe 106 can pass therethrough.

Apart from further components to be described below, the lower half shell 110 receives the two components shown in the exploded view, namely the fixing device 140 and the actuator element 150. However, the components of the lower half shell 110 which are only partially visible in the exploded view of FIG. 10, will be described first in conjunction with FIG. 11.

Figure 11:
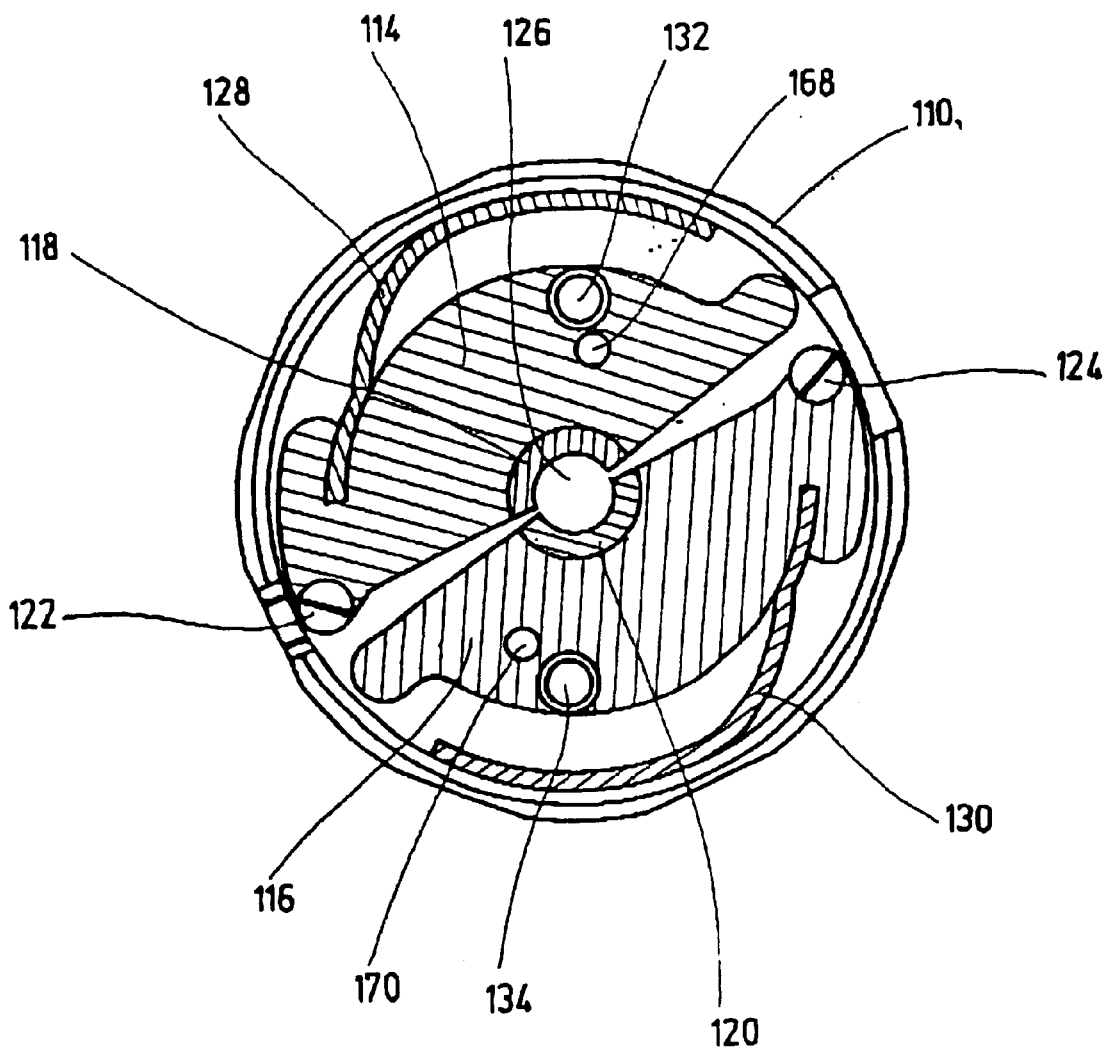
FIG. 11 shows a plan view of the lowermost component shown in FIG. 10 with the moveable clamping elements.

As can be seen from the plan view of FIG. 11, two approximately semicircular plate-like components 114, 116 are arranged in the interior of the half shell 110, which each carry half-cylindrical upstanding clamping elements 118, 120. These two clamping elements 118, 120 oppose one another and form approximately a hollow cylinder when engaging one another. Both the probe 106 and also the inner tube 104 have room in the hollow cylinder, so that it forms a sleeve.

Each of the components 114, 116 is mounted to pivot about a screw 122, 124 in the half shell 110. Each of the components 114, 116 is biased in the housing of the half shell 110 by a spring 128, 130, such that the clamping elements 118, 122 are urged toward one another, i.e. into the clamping position. In this position, they then encompass an inner channel 126.

Each of the components 114, 116 can be pivoted radially outwardly against the force of the corresponding spring 128, 130 about the center axis of the respective screw 112, 124, whereby the clamping elements 118, 120 are moved apart, i.e. into the non-clamping position.

Figure 12:
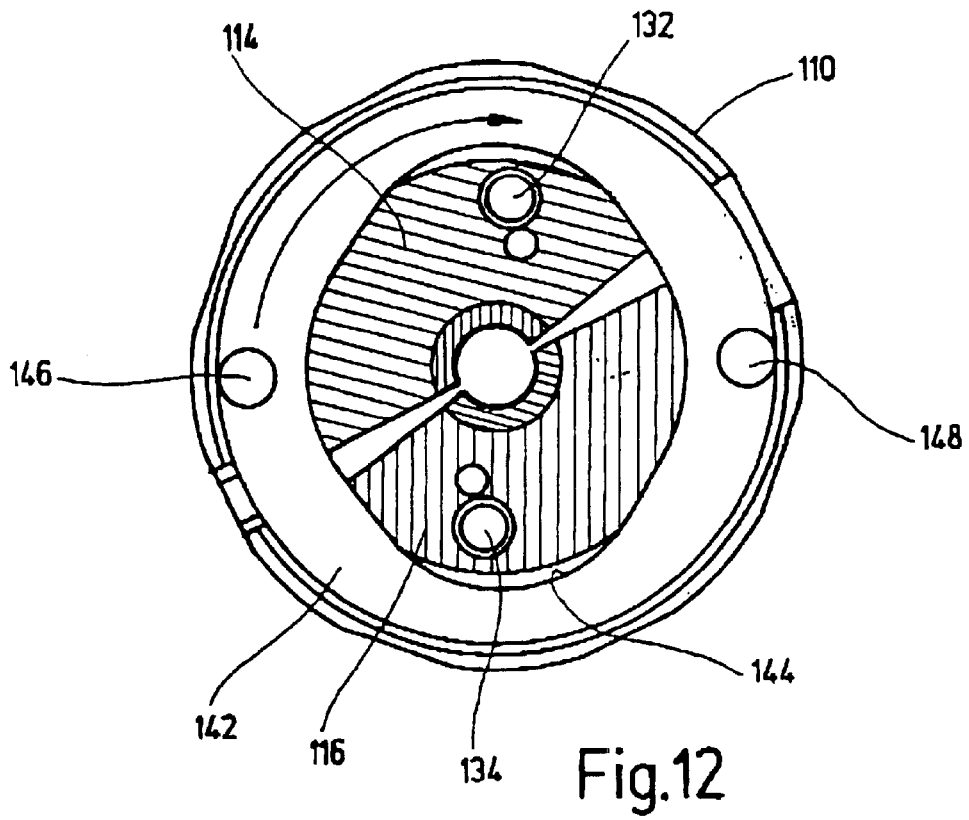
FIG. 12 shows a plan view corresponding to FIG. 11 where the second lowermost component in FIG. 10 is shown, namely the fixing ring.

FIG. 12 shows how the fixing device 140 in the form of a ring 142 is attached to the assembly of FIG. 11. As can be seen, the ring 142 comprises an inner contour 144, which is not circular. Two upstanding pegs 146, 148, located diametrically opposite one another, extend upward from the upper side of the ring 142. In addition, a lock bolt 132, 134 extends upwardly from each of the components 114, 116.

Figure 13:
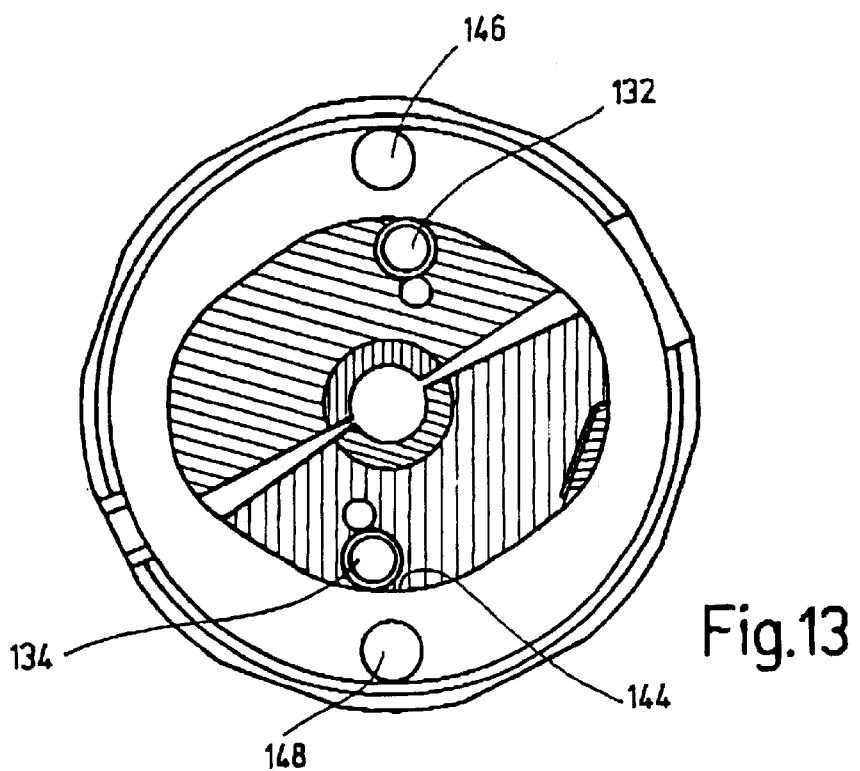
FIG. 13 shows an illustration corresponding to FIG. 12, where the fixing ring is rotated by 90° in clockwise direction.

As can be seen in FIG. 12, a certain radial spacing exists between the lock bolts 132, 134 and the contour 144 of the ring 142, i.e. the components 114, 116 can be spread apart. If the ring 142 is pivoted by 90° in clockwise direction, as indicated in FIG. 12 by the arrow, the ring 142 is brought into the position as shown in FIG. 13.

In this pivoted position, the ring 142 with its inner contour 144 engages both the radially outward side of the lock bolt 132 and also the outside of the lock bolt 134. In this position, the fixing device 140 therefore prevents the clamping elements 118, 120 from being spread apart or from being brought into the non-clamping position. In other words, the fixing device 140 fixes and holds the clamping elements 118, 120 in their clamping position.

Figure 10:
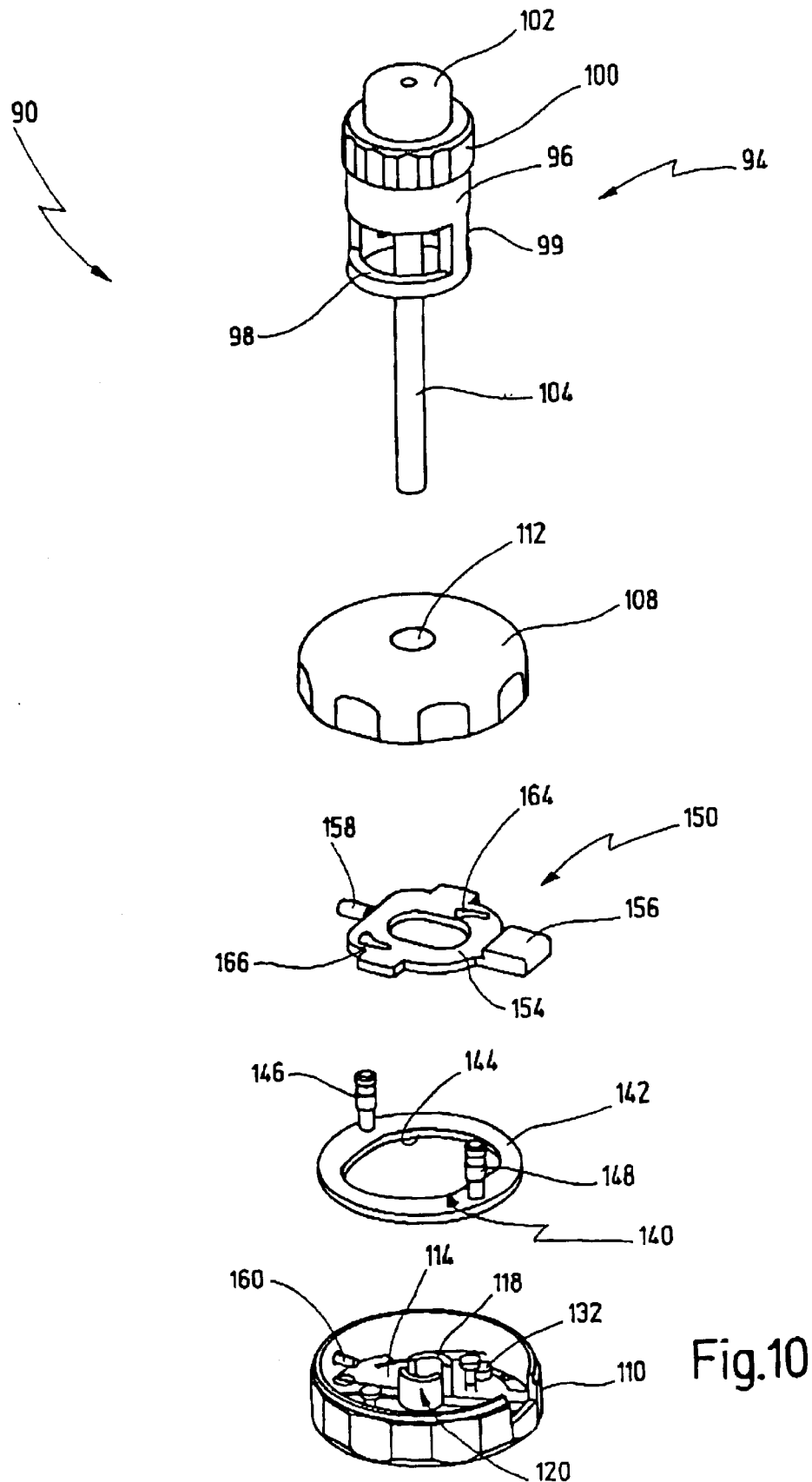
FIG. 10 shows an exploded view of the components of the apparatus of FIG. 9.

As seen in FIG. 10, the two upstanding pegs 146, 148 project from the upper side of the ring 142. These pegs 146, 148 engage and fit into recesses on the underside of the upper half shell 108 which are not seen here. Thus, when the half shell 108 is rotated with respect to the half shell 110, the ring 142 is automatically rotated.

Figure 9:
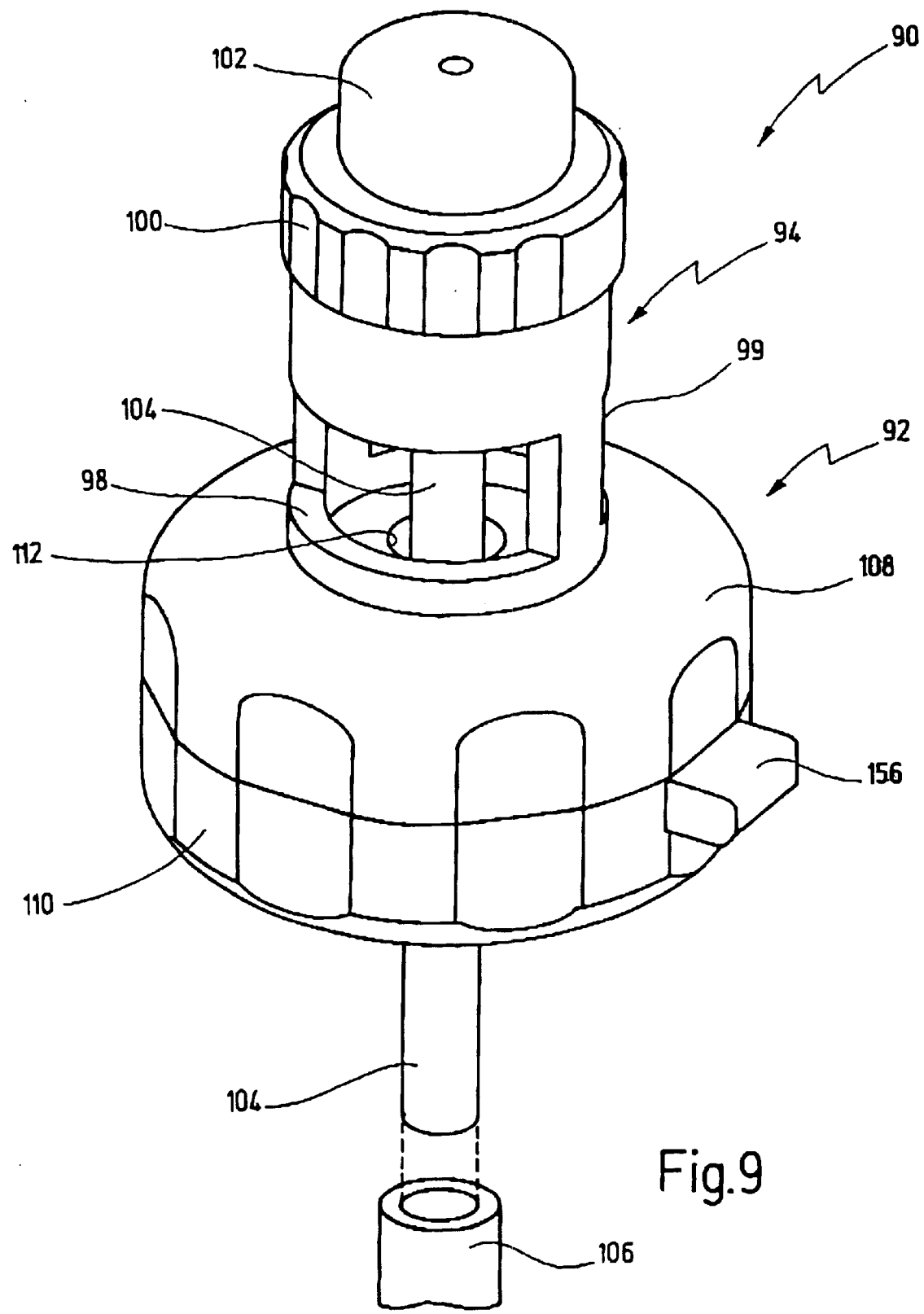
FIG. 9 shows a perspective view of a further embodiment of the present apparatus.
Figure 14:
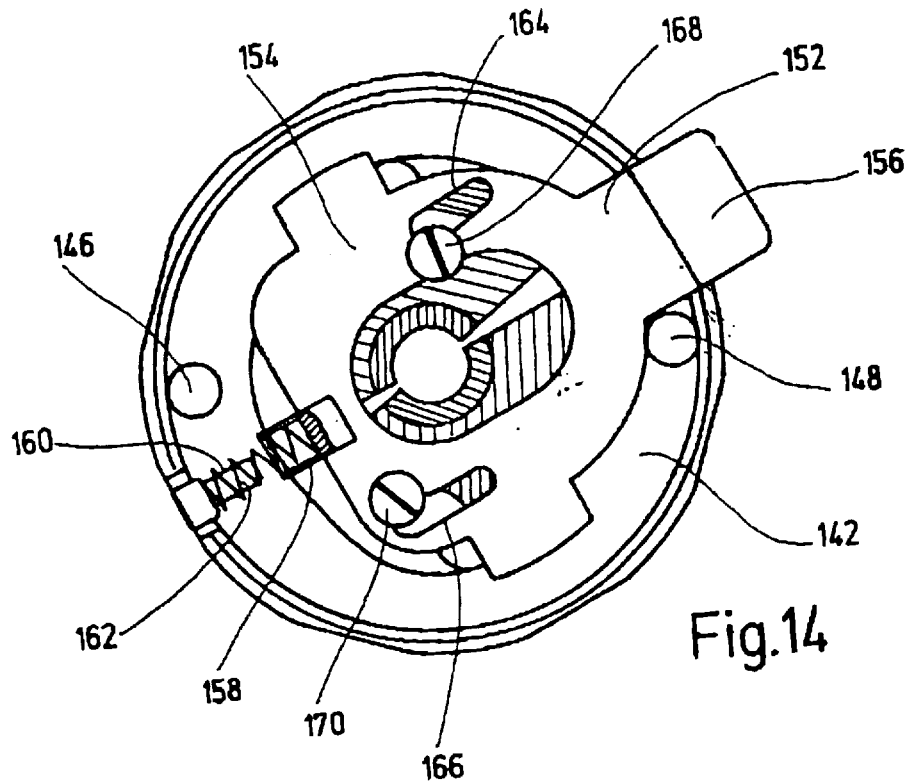
FIG. 14 shows an illustration corresponding to FIG. 12 where the actuator element in the form of a shifter is placed on this assembly, i.e. the component arranged in the middle in the exploded view of FIG. 10.

FIG. 14 shows how the actuator element 150 is additionally attached to the assembly of FIG. 12. The actuator element 150 is formed as a shifter 152 and is formed approximately as a plate 154 with corresponding recesses. The radial extending nose 156, when assembled as shown in FIG. 9, extends from the assembled half shells 108, 110. This provides a point of actuation of the shifter 152 with a finger of one hand. A guide sleeve 158 is provided diametrically opposite the nose (see in particular FIG. 10), which can engage and enclose a corresponding pin 160 at the inner side of the half shell 110.

As seen in the cross-sectional view of FIG. 14, a spring 162 is arranged in the guide sleeve 158 and about the pin 160, which urges the actuator element 150 into the position shown in FIG. 14.

Two slots 164, 166 are provided in the plate 150. Pins 168, 170 extend through the slots, the pins being connected to the lower lying components 114, 116. The contour of the slots 164, 166 is such that the pins 168, 170 are forced radially outwardly when the shifter 152 is pushed radially inwardly as shown with the arrow in FIG. 15. Consequently, the components 114, 116 connected thereto are moved apart from one another and the clamping elements 118, 120 carried by these components are separated or moved into the non-clamping position.

Figure 15:
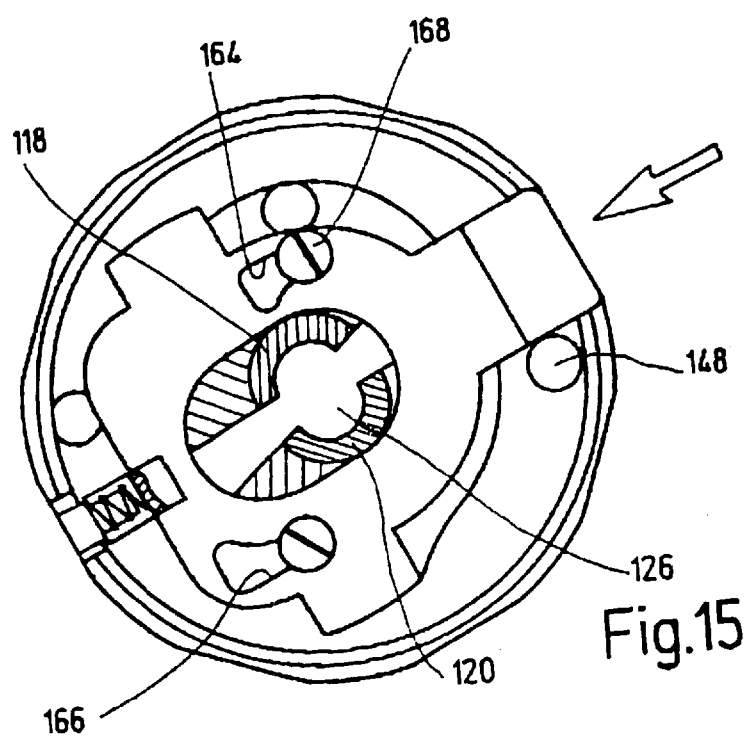
FIG. 15 shows an illustration corresponding to FIG. 14 with the shifter being pushed in, where the clamping elements are brought into a non-clamping position against their biasing.

This is best seen in FIG. 15, i.e. the central channel 126 is widened. In this condition, the probe 106 can be inserted without friction or pushed onto the inner tube 104 arranged in the channel 126 of this assembly. The exact position of the probe 106 can be observed through the windows 98, 99 and after proper seating, the nose 156 of the shifter only need be released and the shifter is then pushed back from the position shown in FIG. 15 to the position shown in FIG. 14. This is promoted by the spring 162 and especially by the two springs 128, 130.

When applying the apparatus 90 to the probe 106, one can for example first pass the assembly of the two half shells 108, 109 over the probe 106 and place the underside of the half shell 110 on the abdominal wall of the patient. The inner tube including the headpiece 94 can then be applied up to a position corresponding to the desired seating. This seating can still be corrected, by temporarily depressing the nose 156 of the shifter 152 and correcting the axial location.

What is claimed is:

1. An apparatus for providing a transcutaneous access to an internal hollow organ of a living body, comprising
    a tubular flexible probe made of a flexible material, said flexible probe being disposed transcutaneously into a hollow organ, a section of said flexible probe extending from said body,
    a rigid sleeve attachable to said section of said probe extending from said body, said rigid sleeve encompassing and engaging said flexible probe in said section, said rigid sleeve having a base for placing said apparatus onto said body, and
    a clamping device for releasingly, but fixedly connecting said flexible probe to said sleeve, said clamping device having moveable clamping elements moveable between a clamping position and a non-clamping position,
    wherein said clamping elements are provided with projections which penetrate into said flexible material of said flexible probe when clamped, however without altering a lumen of said probe.

2. Apparatus of claim 1, wherein said moveable clamping elements are engaging an outer side of said probe in said clamping position.

3. Apparatus of claim 2, wherein said moveable clamping elements are engaging said outer side of said probe over a large area of its surface.

4. Apparatus of claim 1, wherein said base is designed as a component separable from said sleeve.

5. Apparatus of claim 4, wherein said clamping device is arranged within said base.

6. Apparatus of claim 1, wherein said clamping device is provided with two approximately half shell-shaped clamping elements.

7. Apparatus of claim 1, wherein said base is provided with a continuous channel-like opening in which radially moveable clamping elements are arranged.

8. Apparatus of claim 1, wherein said sleeve is provided with a headpiece sealingly attachable to said base.

9. Apparatus of claim 1, wherein said clamping device is provided with a cam shaft rotatable through an outer lever, said cam shaft engaging with at least one of said moveable clamping elements.

10. Apparatus of claim 1, wherein said clamping device is provided with a tube piece through which said probe is passed, and wherein said moveable clamping elements clamping said tube piece in its clamping position such that said probe within said tube piece is clamped.

11. Apparatus of claim 1, wherein said base has a flat base plate.

12. Apparatus of claim 1, wherein said sleeve is provided with a central channel, an interior diameter thereof corresponding to an outer diameter of said probe.

13. Apparatus of claim 1, wherein a valve assembly is provided through which an access created by said probe is sealingly closed.

14. Apparatus of claim 13, wherein a proximal side of said sleeve is closeable via said valve assembly.

15. Apparatus of claim 1, wherein said sleeve is provided with an inner tube which can be inserted into said flexible probe.

16. Apparatus of claim 15, wherein said inner tube extends distally from said base.

17. Apparatus of claim 16, wherein said inner tube extends distally from said base to an extent that it can reach into said internal hollow organ of said living body.

18. Apparatus of claim 1, wherein said sleeve is provided with an inner tube which can be inserted into said flexible probe, said sleeve comprising a headpiece, said inner tube extending to said headpiece.

19. Apparatus of claim 1, wherein said moveable clamping elements being biased in a clamping direction, and wherein an actuator element being provided through which said clamping elements are moveable into said non-clamping position.

20. Apparatus of claim 19, wherein a fixing device is provided which fixes said moveable clamping elements in their clamping position.

21. Apparatus of claim 20, wherein said fixing device has a fixing ring which fixes said moveable clamping elements when disposed at a first angular position and allowing their movement when disposed at a second angular position.

22. Apparatus of claim 21, wherein said base is provided with two shell elements relatively rotatable to one another, and wherein one of said shell elements supports said fixing ring.

23. Apparatus of claim 1, wherein said moveable clamping elements are biased in a clamping direction by a force of springs, and wherein an actuator element being provided through which said clamping elements are moveable into said non-clamping position, and wherein said clamping elements are arranged on components moveable toward said probe biased by said springs, and wherein said actuator element engaging these components such that said clamping elements are moved away from said probe against said force of said springs by actuation of said actuator element.

24. Apparatus of claim 1, wherein said sleeve comprising a headpiece, said headpiece comprising at least one window through which an assembly of said probe and said headpiece can be observed.

* * * * *